United States Patent [19]

Herron et al.

[11] 4,195,021

[45] Mar. 25, 1980

[54] 1,3-DISUBSTITUTED 2-AZETIDINONE ANTIBITOTICS

[75] Inventors: David K. Herron, Indianapolis; Celia A. Whitesitt, Greenwood, both of Ind.

[73] Assignee: Eli Lilly and Company, Indianapolis, Ind.

[21] Appl. No.: 845,766

[22] Filed: Oct. 26, 1977

[51] Int. Cl.$^2$ ................. C07D 205/08; A61K 31/395
[52] U.S. Cl. ............................. 260/239 A; 260/245.4; 260/330.3; 260/347.3; 546/275; 424/244
[58] Field of Search ....... 260/239 AL, 307 H, 308 D, 260/332.2 H, 347.3, 302 H

[56] References Cited

U.S. PATENT DOCUMENTS

| | | | |
|---|---|---|---|
| 3,993,646 | 11/1976 | Kamiya et al. | 260/239 AL |
| 4,058,521 | 11/1977 | Uyeo et al. | 260/239 AL |

FOREIGN PATENT DOCUMENTS

| | | |
|---|---|---|
| 846934 | 4/1977 | Belgium . |
| 849445 | 6/1977 | Belgium . |
| 2529941 | 4/1976 | Fed. Rep. of Germany ... 260/239 AL |

OTHER PUBLICATIONS

Heyningen et al. J. Med. Chem II, 933 (1968).
Sheehan "Tho Synthetic Penicillins", Ad. Chem. #45 (Molecular Modification in Drug Design, American Chem. Society, 1964 p. 15-23.

*Primary Examiner*—Mark L. Berch
*Attorney, Agent, or Firm*—Steven R. Lammert; Arthur R. Whale

[57] ABSTRACT

Novel 3-acylaminoazetidin-4-one antibiotic compounds, prepared by reduction of known 2-chloroazetidin-4-one compounds with tri(butyl)tin hydride, are antinicrobial agents.

14 Claims, No Drawings

1,3-DISUBSTITUTED 2-AZETIDINONE ANTIBITOTICS

BACKGROUND OF THE INVENTION

Penicillin and more recently cephalosporins have gained substantial prominence as medicaments for the treatment of microbial infections. Common to the structure of these two classes of bicyclic antibiotic compounds is a β-lactam ring system. Until the recent discovery of nocardicin, a monocyclic azetidinone compound having the formula

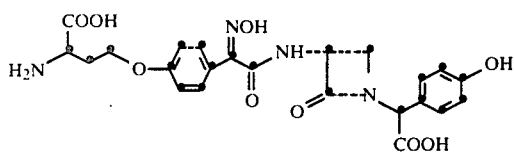

researchers in the area of β-lactam antibiotics have generally believed that a bicyclic β-lactam containing ring structure is essential to achieve the high levels of antibiotic activity characteristic of the clinically significant penicillins and cephalosporins. Although many monocyclic β-lactam compounds have been known, interest in these compounds has been primarily in their use a intermediates to penicillins, cephalosporins and other bicyclic compounds. The recent discovery of nocardicin has prompted investigators to take a closer at monocyclic β-lactam compounds and their antimicrobial activity. The present invention is directed to novel 2-unsubstituted-3-acylaminoazetidin-4-one compounds which exhibit antibiotic activity.

SUMMARY OF THE INVENTION

The present invention provides azetidinone compounds of the formula

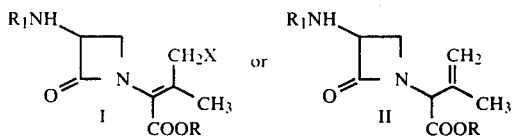

wherein R is hydrogen or a carboxylic acid protecting group; $R_1$ is hydrogen or an acyl group derived from a carboxylic acid; and X is hydrogen, chloro, bromo, $C_1$–$C_3$ acyloxy, hydroxy, $C_1$–$C_4$ alkoxy, benzyloxy, pyridinium or a group of the formula $-SR_3$; which compounds are useful as antimicrobial agents.

The present compounds are derived generally by a tri(butyl)tin hydride reduction of known 2-chloroazetidinone compounds of the formula

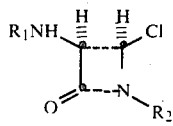

wherein $R_2$ is as defined hereinbelow.

DETAILED-DESCRIPTION OF THE INVENTION

The azetidinones of the present invention are represented by the formula

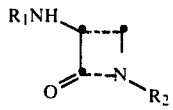

wherein $R_2$ is a group of the formula

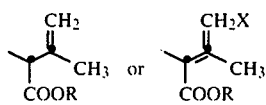

wherein R is hydrogen or a carboxylic acid ester protecting group and
X is hydrogen, chloro, bromo, $C_1$–$C_3$ acyloxy, hydroxy, $C_1$–$C_4$ alkoxy, benzyloxy, pyridinium or a group of the formula $-SR_3$ wherein $R_3$ is $C_1$–$C_4$ alkyl, phenyl, 1-methyl-1,2,3,4-tetrazol-5-yl and 2-methyl-1,3,4-thiadiazol-5-yl; and
wherein $R_1$ is hydrogen or an acyl group of the formula

wherein $R_5$ is
(a) hydrogen, $C_1$–$C_4$ alkyl, halomethyl or phenyl;
(b) benzyloxy, 4-nitrobenzyloxy, 2,2,2-trichloroethoxy, tert-butoxy, or 4-methoxybenzyloxy;
(c) an arylalkyl group of the formula

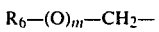

wherein m is 0 or 1 and $R_6$ is 1,4-cyclohexadienyl, phenyl or phenyl substituted with 1 or 2 substituents independently selected from the group consisting of halo, hydroxy, nitro, cyano, trifluoromethyl, $C_1$–$C_4$ alkyl and $C_1$–$C_4$ alkoxy;
(d) a substituted arylalkyl group of the formula

wherein $R_7$ is $R_6$ as defined above, 2-thienyl or 3-thienyl and W is hydroxy, protected hydroxy, carboxy, protected carboxy, amino, protected amino or a group of the formula

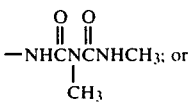

(e) a heteroaryl methyl group of the formula

wherein $R_8$ is 2-thienyl, 3-thienyl, 2-furyl, 2-thiazolyl, 5-tetrazolyl, 1-tetrazolyl or 4-isoxazolyl,
and when $R_1$ is hydrogen, the hydrochloride acid addition salts of the amines represented thereby, and when R is hydrogen the pharmaceutically acceptable salts of the acids represented thereby.

In the foregoing description of the present invention the term $C_1-C_4$ alkoxy refers to the groups methoxy, ethoxy, n-propoxy, isopropoxy, n-butoxy, isobutoxy, and sec-butoxy. Exemplary of $C_1-C_4$ alkyl are methyl, ethyl, isopropyl, n-propyl and n-butyl. "Halomethyl" refers to chloromethyl, bromomethyl or iodomethyl. "$C_1-C_3$ acyloxy" refers to formyloxy, acetoxy, or propionoxy.

Representative of the group $R_6$ when $R_6$ is a substituted phenyl group are 4-hydroxyphenyl, 3-hydroxyphenyl, 3,4-dihydroxyphenyl, 4-chlorophenyl, 3,6-dichlorophenyl, 3,4-dichlorophenyl, 3-bromophenyl, 3-chloro-4-hydroxyphenyl, 3-chloro-4-methylphenyl, 4-tert-butylphenyl, 3,4-dimethylphenyl, 4-ethylphenyl, 3-nitrophenyl, 4-trifluoromethylphenyl, 3-methoxy-4-chlorophenyl, 3-iodophenyl, 2-chloro-3-cyanophenyl, 4-cyanophenyl, 3,4-dimethoxyphenyl, 4-n-butoxyphenyl and 2-propyl-4-methoxyphenyl.

The term "protected amino" as employed in the above definition has reference to an amino group substituted with one of the commonly employed amino blocking groups such as the tert-butoxycarbonyl group (t-BOC); the benzyloxycarbonyl group, the 4-methoxybenzyloxycarbonyl group, the 4-nitrobenzyloxycarbonyl group, the 2,2,2-trichloroethoxycarbonyl group, or the 1-carbomethoxy-2-propenyl group formed with methyl acetoacetate. Like amino protecting groups such as those described by J. W. Barton in "Protective Groups in Organic Chemistry," J. F. W. McOmie, Ed., Plenum Press, New York, N.Y., 1973, Chapter 2 shall be recognized as suitable. The tert-butoxycarbonyl group (t-BOC) and the 4-methoxybenzyloxycarbonyl groups are preferred.

The term "protected hydroxy" has reference to the readily cleavable groups formed with an hydroxyl group such as the formyloxy group, the chloroacetoxy group, the benzyloxy group, the benzhydryloxy group, the trityloxy group, the 4-nitrobenzyloxy group, the trimethylsilyloxy group, the phenacyloxy group, the tert-butoxy group, the methoxymethoxy group, the tetrahydropyranyloxy group, and the like. Other hydroxy protecting groups, including those described by C. B. Reese in "Protective Groups in Organic Chemistry", supra, Chapter 3 shall be considered as within the term "protected hydroxy" as used herein.

The term "carboxylic acid ester protecting group" has reference to the commonly used carboxylic acid protecting groups employed to block or protect the carboxylic acid functionality while reactions involving other functional sites of the compound are carried out. Such carboxy protecting groups are noted for their ease of cleavage by hydrolytic or by hydrogenolytic methods to the corresponding carboxylic acid. Examples of carboxylic acid ester protecting groups include methyl, tert-butyl, benzyl, 4-methoxybenzyl, $C_2-C_6$ alkanoyloxymethyl, 2-iodoethyl, 4-nitrobenzyl, diphenylmethyl (benzhydryl), phenacyl, 4-halophenacyl, dimethylallyl, 2,2,2-trichloroethyl, tri($C_1-C_3$ alkyl)silyl, succinimidomethyl and like ester forming moieties. Other known carboxy protecting groups such as those described by E. Haslam in "Protective Groups in Organic Chemistry", supra, Chapter 5, shall be recognized as suitable. The tert-butyl, 4-methoxybenzyl and the diphenylmethyl carboxy protecting groups are preferred. The term "protected carboxy" has reference to carboxylic acid groups which have been blocked with one of the aforementioned ester forming moieties.

In the foregoing definitions, hydroxy, amino, and carboxy protecting groups are not exhaustively defined. The function of such groups is to protect the reactive functional groups during the preparation of intermediates and then be removed at some later point in time without disrupting the remainder of the molecule. Many such protecting groups are well known in the art. There is no novelty or inventiveness asserted with regard to the "protecting groups" referred to in the description of the present invention.

Representative of the acyl groups

when $R_5$ is a substituted arylalkyl group of the formula

and when W is hydroxy or protected hydroxy are 2-(4-methoxyphenyl)-2-benzyloxyacetyl, 2-(2-thienyl)-2-trimethylsilyloxyacetyl, 2-phenyl-2-benzhydryloxyacetyl, 2-(4-chlorophenyl)-2-formyloxyacetyl, and 2-(2-chloro-4-hydroxyphenyl)-2-hydroxyacetyl. Representative of such groups when W is amino or protected amino are 2-phenyl-2-(4-methoxybenzyloxycarbonylamino)acetyl, 2-(1,4-cyclohexadien-1-yl)-2-benzhydryloxycarbonylaminoacetyl, 2-(4-hydroxyphenyl)-2-(tert-butoxycarbonylamino)acetyl, 2-(3-nitrophenyl)-2-(2,2,2-trichloroethoxycarbonylamino)acetyl, 2-phenyl-2-aminoacetyl, 2-(2-bromo-4-methoxyphenyl)-2-aminoacetyl, and 2-(2-thienyl)-2-aminoacetyl. When W is carboxy or protected carboxy, exemplary acyl groups are 2-(1,4-cyclohexadienyl)-2-carboxyacetyl, 2-phenyl-2-carboxyacetyl, 2-(4-cyanophenyl)-2-(tert-butoxycarbonyl)acetyl, 2-(4-trifluoromethylphenyl)-2-(4-nitrobenzyloxycarbonyl)acetyl, 2-(3-thienyl)-2-carboxyacetyl, 2-(2-thienyl)-2-benzhydryloxycarbonylacetyl, 2-phenyl-2-(2,2,2-trichloroethoxycarbonyl)acetyl, and 2-(4-ethylphenyl)-2-(tert-butoxycarbonyl)acetyl.

The compounds of the present invention are derived from known monocyclic 2-chloro-4-azetidinone compounds of the formula

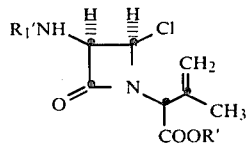

wherein $R_1'$ is an acyl group derived from a carboxylic acid and R' is a carboxy protecting group. The corresponding chloro azetidinone compounds wherein the 2-chloro group is trans to the 3-acylamino group are not suitable starting materials for the present compounds.

The preparation of the cis-chloro azetidinone starting materials represented by the above formula is described in Belgian Pat. No. 832,174.

The preparation of the compounds of the present invention is represented generally by the following reaction scheme:

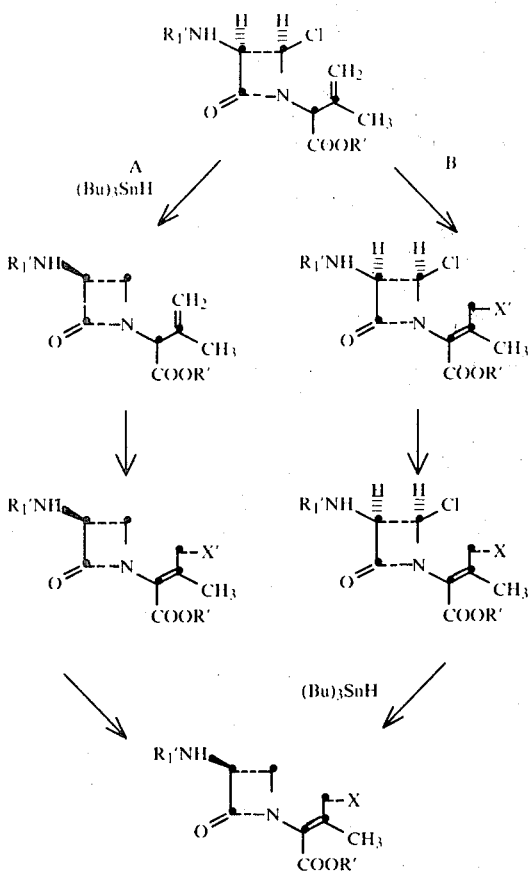

wherein X' is chloro or bromo, R₁' is an acyl group derived from a carboxylic acid and R' is a carboxylic acid protecting group.

In general, therefore, the present compounds of the formula

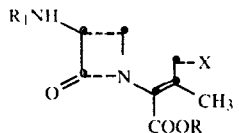

can be prepared by two synthetic routes, each involving identical steps, but differing in the order in which the reaction sequence is carried out.

In one synthetic route (A) to the compounds of the present invention the secondary chloride moiety of the 4-chloroazetidione starting material is first reduced with tri(butyl)tin hydride, and subsequently the butenoate moiety is functionalized as desired. In a second synthetic route (B) to the present compounds, the butenoate moiety is functionalized prior to the tri(butyl)tin hydride reduction step. The first described route has more general application since functional groups (X' or X) introduced prior to the reduction step, could, depending on the nature of such groups, interfere with the free radical type tri(butyl)tin hydride reduction of the secondary chloride functionality. Bromo or chloro groups would be reduced along with the azetidinone C-4 chloro moiety. Also route B would not be acceptable if X were a hydroxy group; the hydroxy group would directly interfere with the desired free radical reduction. For these reasons and others the depicted synthetic route A is preferred for the preparation of the present compounds.

Compounds of the present invention of the formula

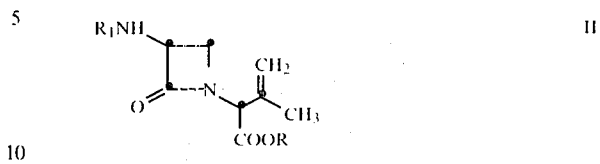

are prepared by reducing of the aforedescribed chloroazetidinone starting materials with tri(butyl)tin hydride, a free radical type reducing agent. The reduction is accomplished by reacting the chloroazetidinone starting material with about a 10% molar excess of tri(butyl)tin hydride in the presence of about an equivalent amount of a free radical initiator such as di-tert-butylperoxide or azobisisobutyronitrile in a dry inert organic solvent at about 50° to about 90° C. Typically the reaction is carried out by heating a mixture of the chloroazetidinone starting material, a molar equivalent amount of azobisisobutyronitrile and a 10% molar excess of tri(butyl)tin hydride in dry benzene or toluene to about 65° C. for about 3 to about 20 hours. To assure dry reaction conditions the reduction is preferably carried out under a dry nitrogen atmosphere. The reaction is typically complete after about 4 to about 6 hours. The progress of the reaction can be easily followed by comparative thin-layer chromatography.

The product 2-unsubstituted azetidin-4-ones can be isolated by conventional laboratory separation and purification methods. For example, the product resulting from the reduction of benzhydryl 2-(3-phenoxyacetamido-2-chloro-4-azetidin-1-yl)-3-methyl-2-butenoate with tri(butyl)tin hydride/azobisisobutyronitrile in toluene at 65° C. for 4 hours crystallizes from the reaction mixture upon cooling.

Because of the nature of the free radical reduction employed in the preparation of the present compounds, precaution must be taken not to select chloroazetidinone starting materials which bear substituents which would interfere with the free radical reduction of the secondary chloride functionality or which would be susceptible to reduction themselves under the reaction conditions. Thus protecting groups derived from, for example, the 2-iodoethyl group, the 4-nitrobenzyl group, or the 2,2,2-trichloroethyl group should be avoided for the initial free radical reduction step in preparing the present compounds since such groups are susceptible in varying degrees to reductive reaction conditions. In contrast, protecting groups derived from the 4-methoxybenzyl group, the tert-butyl group and the diphenylmethyl (benzhydryl) group, which are known acid labile protecting groups, have been found to be especially stable under the tri(butyl)tin hydride conditions and are preferred. Carboxy protecting groups derived from the benzhydryl group are most preferred.

Free amino, hydroxy, and carboxy groups serve as "radical traps" and therefore would directly interfere with the desired free radical reduction. Such groups, if present on the chloroazetidinone starting material, must first be protected with one of the conventional protecting groups (other than one of those aforedescribed reduction-labile protecting groups) prior to carrying out the tri(butyl)tin hydride reduction.

Thus, for example, 2-[3S-(2-phenyl-2-aminoacetamido)-4R-chloro-2-oxoazetidin-1-yl]-3-methyl-3-butenoic acid of the formula

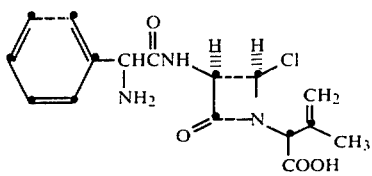

can be converted to the corresponding 4-unsubstituted azetidinone compound of the present invention by (1) esterifying the carboxy functionality with diphenyldiazomethane to provide the benzhydryl ester; (2) protecting the side chain amino group with the tert-butoxycarbonyl group by reacting the amino ester with tert-butoxy chloroformate or tert-butoxy azidoformate; (3) reducing the secondary chloride moiety with tri(butyl)tin hydride in the presence of azobisisobutyronitrile to afford the protected 4-unsubstituted azetidinone, also a compound of the present invention; and (4) reacting the protected azetidinone with trifluoroacetic acid in the presence of anisole, a well known method of removing both the benzhydryl ester protecting group and the tert-butoxycarbonyl amino protecting group.

Preferred starting materials for the preparation of the compounds of the present invention are the diphenylmethyl (benzhydryl), 4-methoxybenzyl and tert-butyl ester of 2-(3S-phenylacetamido-4R-chloro-2-oxoazetidin-1-yl)-3-methyl-3-butenoic acid and 2-(3-S-phenoxyacetamido-4R-chloro-2-oxoazetidin-1-yl)-3-methyl-3-butenoic acid.

The azetidinone C-3 acylamino side chain moiety can be cleaved after the tri(butyl)tin hydride reduction process by using well known phosphorous pentachloride/pyridine/isobutanol cleavage conditions to provide the corresponding azetidinone C-3 amino compounds and their hydrochloric acid addition salts, also compounds of the present invention. The C-3 amino derivatives can then be reacylated in accordance with conventional acylation procedures, typically using activated forms-acid chlorides, mixed anhydrides, or active esters-of carboxylic acids to provide a broad scope of C-3 acylamino derivatives analogous to the scope of C-6 and C-7 acylamino side chains which have been described in the penicillin and cephalosporin art. Similarly those carboxy protecting groups preferred for the reduction step can be removed by acid hydrolysis and replaced with other known carboxy protecting groups which can be employed in carrying out the subsequent conversions on the butenoate moiety described hereinbelow.

The 2-(3-acylamino-2-oxoazetidin-1-yl)-3-methyl-2-butenoate esters (formula I, X=H) of the present invention are derived from the corresponding 3-butenoate esters (formula II) by a base induced isomerization of the double bond in the 3-butenoate compounds. The reaction is typically carried out at room temperature in an inert organic solvent such as chloroform, methylene chloride, 1,2-dichloroethane, tetrahydrofuran or ethylacetate using about an equivalent amount of a tertiary amine base. 4-Methoxybenzyl 2-[3-(2-thienylacetamido)-2-oxoazetidin-1-yl]-3-methyl-2-butenoate, for example, can be prepared by reacting the corresponding 3-butenoate compound with an equivalent amount of triethylamine in methylene chloride at room temperature for two hours. Isolation and purification of the product is accomplished by conventional laboratory procedures.

The present azetidinone compounds of formula I wherein X is bromo or chloro are derived from the 3-butenoate compounds of formula II using the general procedures described in U.S. Pat. No. 4,042,585, issued Aug. 16, 1977, which discloses a process for preparing 3-halomethylcephems by reaction of 3-exomethylene cephams with an alkali metal salt of a $C_1-C_7$ alcohol or a bicyclic amidine base in the presence of a halogenating agent at a temperature ranging from $-80°$ to about $20°$ C. Thus, compounds of the present invention wherein X is bromo are prepared by reacting the corresponding 3-butenoate compound with about 2 equivalents 1,5-diazobicyclo[5.4.0]undecene-5(DBU) in the presence of about 2 equivalents of bromine in tetrahydrofuran at about $-78°$ C. Preferably a halogen reducing agent, such as aqueous sodium bisulfite or sodium thiosulfite, is added to the reaction mixture before it is allowed to warm to room temperature to destroy excess halogenating agent and therefore preclude further undesirable side reactions at the warmer temperatures. The preparation of the present compounds of formula I above wherein X is chloro is accomplished using an identical procedure except that tert-butyl hypochlorite is employed as the halogenating agent instead of bromine.

Halogenation of the 3-butenoate moiety under the above described reaction conditions provides a mixture of geometrical isomers wherein the halomethyl group is either cis or trans to the carboxy substituent on the butenoate double bond. Although the isomers can be separated by conventional chromatographic means, the isomeric mixture itself is typically employed as the starting material for the subsequent conversions described hereinbelow wherein the allylic halo group is replaced by other substituents. The major product isolated in each of the described displacement reactions has been assigned the structures indicated the trans geometrical isomer.

Exemplary of the 4-chloro and 4-bromo-2-butenoate compounds of the present invention are:

benzhydryl 2-(3-acetamido-2-oxoazetidin-1-yl)-3-methyl-4-chloro-2-butenoate,

2',2',2'-trichloroethyl 2-[3-(nitrobenzyloxycarbonylamino)-2-oxoazetidin-1-yl]-3-methyl-4-bromo-2-butenoate, 4'-nitrobenzyl 2-(3-chloroacetamido-2-oxoazetidin-1-yl)-3-methyl-4-bromo-2-butenoate, tert-butyl 2-(3-benzamido-2-oxozetidin-1-yl)-3-methyl-4-chloro-2-butenoate, 4-methoxybenzyl 2-[3-(5-tetrazolylacetamido)-2-oxoazetidin-1-yl]-3-methyl-4-chloro-2-butenoate, 2'-iodoethyl 2-[3-[2-(4-hydroxyphenyl)-2-formyloxyacetamido]-2-oxoazetidin-1-yl]-3-methyl-4-bromo-2-butenoate, and phenacyl 2-[3-(4-chlorophenoxyacetamido)-2-oxoazetidin-1-yl]-3-methyl-4-bromo-2-butenoate.

The ester protecting groups can be removed by conventional means from the resulting 4-chloro or 4-bromo-2-butenoate derivatives to provide biologically active oxoazetidinyl butenoic acid compounds of the present invention. However the 3-chloro and especially the 3-bromo-2-butenoate ester derivatives are themselves also useful for preparing other compounds of the present invention.

The compounds of the present invention of the formula

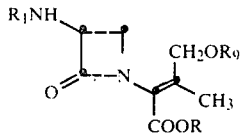

wherein $R_9$ is $C_1$-$C_4$ alkyl or benzyl are prepared by reacting preferably the 3-bromo-2-butenoates described immediately hereinabove with a silver salt such as silver nitrate, silver perchlorate or silver tetrafluoroborate in the presence of a $C_1$-$C_4$ alcohol or benzyl alcohol. Typically a 2-fold excess of the silver salt is employed while the alcohol is used either as the reaction medium or as a cosolvent with an inert organic solvent such as tetrahydrofuran, dioxane or ethyl acetate to comprise the reaction medium. The reaction is carried out at about 0° C. for about 1 hour. The products are isolated and purified chromatographically.

Compounds of the present invention of formula I wherein X is $C_1$-$C_3$ acyloxy, pyridinium or a group of the formula —$SR_3$ are prepared by nucleophilic displacement of the bromo moiety from the corresponding compounds wherein X is bromo. Thus the formyloxy, the acetoxy and the propionoxy groups can be introduced by reacting salts of the corresponding carboxylic acids with the 4-bromo-2-butenoates in an inert organic solvent such as methylene chloride, dimethylformamide, dimethylsulfoxide, or a hexamethylphosphoramide (HMPA). Alkali metal salts or the salts formed with tetramethylguanadine are suitable. The displacement reaction is generally conducted at 0° C. to room temperature using a 3 to 5 fold excess of the carboxylic acid salt.

Reaction of the aforedescribed 4-bromo-2-butenoate with mercaptans provides the compounds of the present invention wherein X is a group of the formula —$SR_3$. The reaction conditions are similar to those described above for the preparation of the corresponding acyloxy compounds. Typically, however, only a slight excess of the mercapto reagent is required. Thus, for example, benzhydryl 2-[3-(2-thienylacetamido)-2-oxoazetidin-1-yl]-3-methyl-4-isopropylthio-2-butenoate can be prepared by reacting benzhydryl 2-[3-(2-thienylacetamido)-2-oxoazetidin-1-yl]-3-methyl-4-bromo-2-butenoate with 1.1 equivalents of isopropyl thiol in dimethylformamide for 1 hour at 0° C. Optionally propylene oxide can be added to the reaction mixture to eliminate the acid liberated during the reaction.

Suitable mercapto compounds which can be employed in preparing the present compounds are methylthiol, ethylthiol, propan-2-thiol, butan-2-thiol, phenylthiol, 5-mercapto-1,2,3,4-tetrazole, and 5-mercapto-2-methyl-1,3,4-thiadiazole.

Pyridinium compounds of the present invention wherein

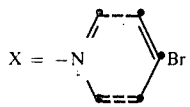

are provided by reacting equivalent amounts of the corresponding allylic bromo compound and pyridine in a dry inert organic solvent such as methylene chloride or tetrahydrofuran at room temperature. For example, 4-methoxybenzyl 2-[3-(5-tetrazolylacetamido)-2-oxoazetidin-1-yl]-3-methyl-4-bromo-2-butenoate can be reacted with pyridine in dry tetrahydrofuran at room temperature to provide 4-methoxybenzyl 2-[3-(5-tetrazolylacetamido)-2-oxoazetidin-1-yl]-3-methyl-4-pyridinium-2-butenoate bromide. Cleavage of the 4-methoxybenzyl ester with trifluoroacetic acid/anisole at 0° provides 2-[3-(5-tetrazolylacetamido)-2-oxoazetidin-1-yl]-3-methyl-4-pyridinium-2-butenoic acid trifluoroacetate

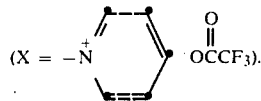

It will be appreciated by those skilled in the art that the pyridinium moiety on the pyridinium compounds of the present invention can be associated with a wide variety of anions or anionic radicals derived from both organic and inorganic acids. The particular anion or anionic radical associated with the pyridinium moiety is dependent on the method of preparing and isolating the pyridinium compounds. Intramolecular salts-zwitter ions-involving the pyridinium and the carboxylate functionalities can also be prepared.

Compounds of the present invention of the formula

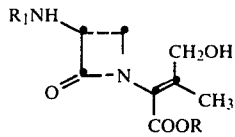

are prepared by aqueous hydrolysis of the corresponding formyloxy compounds

under basic conditions. Typically the hydrolysis is accomplished by adding a cold solution of the formyloxy precursor in cold (0° C.) tetrahydrofuran to an equivalent amount of cold aqueous sodium hydroxide. Thus tert-butyl 2-(3-phenylacetamido-2-oxoazetidin-1-yl)-3-methyl-4-hydroxy-2-butenoate is provided by stirring a solution of tert-butyl 2-(3-phenylacetamido-2-oxoazetidin-1-yl)-3-methyl-4-formyloxy-2-butenoate in cold tetrahydrofuran with an equivalent amount of 1 N. aqueous sodium hydroxide at ice bath temperature for about 30 minutes. The product can be isolated by standard laboratory techniques and purified by preparative thin layer chromatography.

The aforedescribed 2-(3-acylamino-2-oxoazetidin-1-yl)-3-methylbutenoates of the present invention can be converted to the corresponding 2-(3-amino-2-oxoazetidin-1-yl)-3-methylbutenoates, and their hydrochloride acid addition salts, also compounds of the present invention, using the well known phosphorous pentachloride amide cleavage reaction. The reaction proceeds via the imidoyl chloride which is thereafter converted to the imino ether using a lower alcohol such as methanol, ethanol, or isobutanol. The imino ether hydrolyzes to provide either the free amine or its hydrochloride salt depending on the method of hydrolysis and isolation procedures. Thus 4'-nitrobenzyl 2-[3-(2-thienylacetamido)-2-oxoazetidin-1-yl]-3-methyl-4-chloro-2-butenoate when reacted with 1.1 equivalents of phosphorous pentachloride and 1.1 equivalents of pyridine in methylene chloride at 0° provides the corresponding imidoyl chloride which is reacted with excess isobutanol to give the corresponding imino ether. The imino ether hydrolyzes under the reaction conditions to provide the corresponding 4'-nitrobenzyl-2-(3-amino-2-oxoazetidin-1-yl)-3-methyl-4-chloro-2-butenoate hydrochloride which precipitates upon the addition to the reaction mixture of a large excess of diethyl ether. Alternatively water can be added to the imido ether solution to promote hydrolysis of the imino ether. Following conventional laboratory procedures the corresponding free amine can be isolated.

Representative of the compounds of the present invention wherein $R_1$ is hydrogen are tert-butyl 2-(3-amino-2-oxoazetidin-1-yl)-3-methyl-3-butenoate, 2',2',2'-trichloroethyl 2-(3-amino-2-oxoazetidin-1-yl)-3-methyl-4-acetoxy-2-butenoate, benzhydryl 2-(3-amino-2-oxoazetidin-1-yl)-3-methyl-4-bromo-2-butenoate, 4'-nitrobenzyl 2-(3-amino-2-oxoazetidin-1-yl)-3-methyl-4-phenylthio-2-butenoate, 4'-methoxybenzyl 2-(3-amino-2-oxoazetidin-1-yl)-3-methyl-4-isopropoxy-2-butenoate and the hydrochloride acid addition salts thereof.

The aforedescribed amino esters are useful in preparing corresponding acylamino esters wherein the particular acyl group is such that it is advantageous or desirable to carry out the tri(butyl)tin hydride reduction and the modifications of the butenoate moiety using more readily available starting materials and subsequently modifying the acylamino as the last step in preparing the desired compounds.

The amino ester derivatives of the present invention are acylated in accordance with well known procedures. The acylation can be carried out with an active derivative of the carboxylic acid $R_5COOH$ wherein $R_5$ is as defined above. Of course, any functional groups on the carboxylic acid moiety which could interfere with the acylation reaction such as free hydroxy, carboxy or amino groups should be first protected with one of the aforedescribed protecting groups. Active derivatives of these acids include the acyl halides such as the acid chlorides or bromides, the acid azides, and the mixed anhydrides formed with methyl chloroformate, ethyl chloroformate or isobutyl chloroformate. The acylation can be carried out with the free carboxylic acid with a condensing agent such as dicyclohexylcarbodiimide as described in U.S. Pat. No. 3,218,318. Also the acylation can be effectuated using the active ester formed by the reaction of the carboxylic acid ($R_5COOH$) and 1-hydroxybenzotriazole in the presence of dicyclohexylcarbodiimide as a condensing agent.

Removal of the carboxylic acid protecting group and any protecting groups employed to temporarily block functional groups on the side chain moiety provides the compounds of this invention that are useful antibiotics which inhibit the growth of pathogenic microorganisms. Methods for removal of these groups are well known and are described in the literature.

The azetidinone antibiotics of the present invention have a carboxylic acid group which forms salts with suitable bases. Pharmaceutically acceptable salts include the alkali metal salts such as the sodium, potassium and lithium salts; the calcium salt and salts formed with pharmaceutically acceptable amines such as methylamine, dimethylamine, cyclohexylamine, dicyclohexylamine, ethanolamine, diethanolamine, dibenzylamine and tris(hydroxymethyl)aminomethane.

The carboxylic acids of this invention are useful in combatting infections in warm blooded mammals when formulated in liquid form, e.g. in water or isotonic saline and administered parenterally, for example, subcutaneously, intramuscularly or intravenously preferably in the form of a pharmaceutically acceptable non-toxic salt in doses between about 100 and about 500 mg/kg of body weight. Alternatively the carboxylic acid salts of this invention can be formulated in liquid form, for example, in water at concentrations of about 10 to about 50 g. per liter and used to disinfect inanimate objects, such as items of dental and medical equipment.

The following examples are provided to further describe the compounds of the present invention and their preparation.

EXAMPLE 1

Benzhydryl 2-(3-phenoxyacetamido-2-oxoazetidin-1-yl)-3-methyl-3-butenoate

A mixture of 6.83 g (13 mmol) of benzhydryl 2-(3S-phenoxyacetamido-4R-chloro-2-oxoazetidin-1-yl)-3-methyl-3-butenoate, 2.15 g (13.1 mmol) of azobisisobutyronitrile and 3.7 ml (14.8 mmol) tri(n-butyl)tin hydride in 13 ml of toluene was heated for 4 hours at 65° C. Upon cooling the product crystallized. The product was filtered and then slurried with 100 ml of diethyl ether for ½ hour. Filtration provided 5.2 g (82%) of the title product: nmr (CDCl$_3$) δ 1.83 (3, s, —CH$_3$), 4.82 (s, 1, -CHCOOR), 5.08 (s, 2, =CH$_2$), 3.85 (t, 1) and 3.38 (q, 1) [azetidinone C$_4$-protons], 4.81 (m, 1, C$_3$—H), 4.45 (s, 2, —OCH$_2$CO—), and 7.2 (b, 15, ArH).

EXAMPLE 2

Benzhydryl 2-(3-phenoxyacetamido-2-oxoazetidin-1-yl)-3-methyl-2-butenoate

To a solution of 50 mg of benzhydryl 2-(3-phenoxyacetamido-2-oxoazetidin-1-yl)-3-methyl-3-butenoate in 10 ml of methylene chloride was added 3 drops of triethylamine. After 2 hours at room temperature the reaction mixture was washed thoroughly with brine and dilute acid. After drying, the solution was evaporated in vacuo to dryness to provide 50 mg of the title product: nmr (CDCl$_3$) δ 2.05 (s, 3, CH$_3$), 2.25 (s, 3, CH$_3$), 3.60 (2, m, azetidinone C$_4$—H), 5.02 (m, 1, C$_3$—H), 4.55 (s, 2, —OCH$_2$CO—), and 7.2 (b, 15, ArH).

EXAMPLE 3

2-(3-Phenoxyacetamido-2-oxoazetidin-1-yl)-3-methyl-2-butenoic acid

Benzhydryl 2-(3-phenoxyacetamido-2-oxoazetidin-1-yl)-3-methyl-2-butenoate (100 mg) was dissolved in a mixture of 2 ml of anisole and 1 ml of trifluoroacetic acid at 0°. After 10 minutes 50 ml of hexane was added. The residue obtained by evaporating the solution in vacuo to dryness was taken up in ethyl acetate and the resulting solution was layered with water. After the pH of the aqueous layer was adjusted to 8.5, the aqueous layer was separated and layered with ethyl acetate. The pH of the aqueous layer was then adjusted to 2.5. The organic layer was separated, dried and evaporated to dryness in vacuo to provide 23 mg of the title product: nmr (CDCl$_3$) δ 1.98 (s, 3, CH$_3$), 2.17 (s, 3, CH$_3$), 3.60 (m, 2, C$_4$—H), 4.98 (m, 1, C$_3$—H), 4.60 (s, 2, —OCH$_2$CO), and 7.2 (b, 5, ArH).

EXAMPLE 4

Benzhydryl 2-(3-amino-2-oxoazetidin-1-yl)-3-methyl-2-butenoate hydrochloride

Approximately 2 mmol of benzhydryl 2-(3-phenoxyacetamido-2-oxoazetidin-1-yl)-3-methyl-2-butenoate was dissolved in 10 ml of methylene chloride at 0° with 0.193 ml pyridine (2.4 mmol). To the cold, stirred solution was added 458 mg (2.2 mmol) of phosphorous pentachloride. The reaction was stirred for 2 hours while it was allowed to warm to about 10°. The solution was then cooled to 0° and 0.2 ml of isobutanol was added. After stirring for 1 hour at 0°, ether (50 ml) was slowly added. The supernatant liquid was decanted from the oily product that formed. Trituration with ether provided 800 mg of the title amino ester: nmr (CDCl$_3$) δ 2.10 (2, 3, CH$_3$), 1.95 (s, 3, CH$_3$), 3.87 (m, 2, C$_4$—H), 4.70 (m, 1, C$_3$—H) and 7.2 (b, 10, ArH).

EXAMPLE 5

Benzhydryl 2-[3-[D-2-(4-hydroxyphenyl)-2-tert-butoxycarbonylaminoacetamido]-2-oxoazetidin-1-yl]-3-methyl-2-butenoate The amino ester from Example 4 above was dissolved in 8 ml of acetonitrile and 2 ml of bistrimethylsilylacetamide was added. Evaporation of the mixture to dryness provided the silylated nucleus ester which was dissolved in 2 ml of tetrahydrofuran (THF). Hydroxybenzotriazole (306 mg, 2 mmol) and tert-butoxycarbonyl-D-4-hydroxyphenylglycine (534 mg, 2 mmol) were dissolved in 4 ml of tetrahydrofuran. The solution was cooled to 0° and 453 mg (2 mmol) of dicyclohexylcarbodiimide was added. After stirring for 2 hours at room temperature, the reaction mixture was filtered. To the filtrate was added the previously prepared THF solution of the silylated nucleus ester. The mixture was stirred for 4 hours at room temperature. The residue obtained upon evaporation of the reaction solvent was dissolved in ethyl acetate, and the resulting solution was washed successively with brine, aqueous sodium bicarbonate, and dilute acid. The organic layer was dried and evaporated in vacuo to dryness to provide 400 mg of the title product: nmr (CDCl$_3$) δ 1.42 (s, 9, tert-butyl), 2.18 (s, 3, CH$_3$), 2.00 (s, 3, CH$_3$), 3.68 (t, 1) and 3.50 (q, 1) [azetidinone C$_4$—H], 4.95 (m, 1, C$_3$—H), 5.12 (d, 1, side chain CH), and 7.2 (b, 14, ArH).

EXAMPLE 6

2-[3-[D-2-(4-hydroxyphenyl)-2-aminoacetamido]-2-oxoazetidin-1-yl]-3-methyl-2-butenoic acid trifluoracetic acid salt The product from Example 5 above was dissolved in 1 ml. of anisole at 0°, and 1 ml. of cold trifluoracetic acid was added. After 15 minutes at 0°, 50 ml of hexane was added. The residue obtained by evaporating the solvents from the reaction mixture was dissolved in 2 ml of cold trifluoroacetic acid. After 15 minutes the trifluoroacetic acid was evaporated in vacuo. The residue was triturated with ether and filtered to provide 210 mg of the title product: nmr (acetone d-6) δ 2.18 (s, 3, CH$_3$), 2.00 (s, 3, CH$_3$), 3.63 (m, 2, C$_4$—H), 4.92 (m, 1, C$_3$—H), 5.13 (1, side chain CH), and 7.2 (b, ArH).

EXAMPLE 7

Benzhydryl 2-(3-phenoxyacetamido-2-oxoazetidin-1-yl)-3-methyl-4-bromo-2-butenoate To a solution of 4.1 ml of 1,5-diazabicyclo[5.4.0]undecene-5 (DBU) and 1.6 ml of bromine in 90 ml of tetrahydrofuran (THF) at −78° was added 4.36 g (9.0 mmol) of benzhydryl 2-(3-phenoxyacetamido-2-oxoazetidin-1-yl)-3-methyl-3-butenoate in 20 ml of THF. The reaction mixture was placed in an ice bath and stirred for 20 minutes. Sodium bisulfite (3 g) in 30 ml of water was then added. After 10 min. the THF was removed under reduced pressure. Ethyl acetate was added to the resulting aqueous mixture. The organic layer was washed with dilute acid, sodium bicarbonate solution and brine (2X), dried, and evaporated in vacuo to provide 3.6 g (77%) of the title product: nmr (CDCl$_3$) δ 2.13 and 2.28 (s, 3, CH$_3$), 4.2 (m, 2, —CH$_2$Br), 3.67 (m, 2, C$_4$—H), 4.97 (m, 1, C$_3$—H), 4.50 (s, 2, side chain CH$_2$), and 7.2 (b, ArH).

EXAMPLE 8

Benzhydryl 2-(3-phenoxyacetamido-2-oxoazetidin-1-yl)-3-methyl-4-methoxy-2-butenoate (A) To a solution of 281 mg (0.5 mmol) of benzhydryl 2-(3-phenoxyacetamido-2-oxoazetidin-1-yl)-3-methyl-4-bromo-2-butenoate in 10 ml of methanol at 0° was added 207 mg (1 mmol) of silver perchlorate. The reaction mixture was stirred for 1 hour. A large amount of ethyl acetate was added. The resulting solution was washed thoroughly with brine, dried, and evaporated in vacuo to dryness to provide a mixture of the title product and benzhydryl 2-(3-phenoxyacetamido-2-oxoazetidin-1-yl)-2-methoxy-3-methyl-3-butenoate. The products were separated by preparative thin layer chromatography (silica gel plates developed with 1:1/hexane:ethylacetate). A purified sample of 46 mg of the title product was isolated: nmr (CDCl$_3$) δ 2.20 (s, 3, CH$_3$), 3.25 (s, 3, OCH$_3$), 4.37 (s, 2, CH$_2$OCH$_3$), 3.73 (t, 1) and 3.50 (q, 1) [C$_4$—H], 4.97 (m, 1, C$_3$—H), 4.47 (s, 2, side chain CH$_2$) and 7.2 (b, ArH).

(B) Benzhydryl 2-(3-phenoxyacetamido-4-chloro-2-oxoazetidin-1-yl)-3-methyl-4-methoxy-2-butenoate [prepared from benzhydryl 2-(3-phenoxyacetamido-4-chloro-2oxoazetidin-1-yl)-3-methyl-2-butenoate using the general procedures described in Examples 7 and 8(A) hereinabove] (264 mg, 0.5 mmol) was dissolved in 1 ml of toluene with 0.6 mmol of tri(butyl)tin hydride and 0.6 mmol of azobisisobutyronitrile (99 mg) and heated at 62° with stirring under a nitrogen atmosphere. The reaction solvent was removed under reduced pressure to provide an impure product which was purified by preparative thin layer chromatography. (1:2/ethyl acetate:hexane). Yield —54 mg of title product.

EXAMPLE 9

2-(3-Phenoxyacetamido-2-oxoazetidin-1-yl)-3-methyl-4-methoxy-2-butenoic acid

Benzhydryl 2-(3-phenoxyacetamido-2-oxoazetidin-1-yl)-3-methyl-4-methoxy-2-butenoate (200 mg) was dissolved in 1 ml of 1:1 mixture of anisole and trifluoracetic acid at 0°. After 30 min. at 0°, 50 ml of hexane was added and the solvents were removed under reduced pressure. The residue thereby obtained was washed thoroughly with ether and dried. A total of 53 mg of the title product was isolated: nmr (CDCl$_3$) δ 2.07 (s, 3, CH$_3$), 3.33 (s, 3, —OCH$_3$), 4.33 (s, 2, —C$\underline{H}_2$OCH$_3$), 3.77 (m, 2, C$_4$—H), 5.00 (m, 1, C$_3$—H), 4.52 (s, 2, side chain CH$_2$) and 7.2 (b, ArH).

EXAMPLE 10

Benzhydryl 2-(3-amino-2-oxoazetidin-1-yl)-3-methyl-4-methoxy-2-butenoate hydrochloride To a solution of 600 mg (1.1 mmol) of benzhydryl 2-(3-phenoxyacetamido-2-oxoazetidin-1-yl)-3-methyl-4-methoxy-2-butenoate and 0.106 ml pyridine in 10 ml of methylene chloride at 0° was added 252 mg (1.32 mmol) of phosphorous pentachloride. The reaction mixture was stirred for 2 hours while it was allowed to warm to 10°. The solution was then cooled to 0° and 0.2 ml of isobutanol was added. After 1 hour at 0°, 150 ml of ether was slowly added. The supernatant liquid was then decanted from the resulting oily residue, which was itself then thoroughly triturated with ether: nmr (CDCl$_3$) δ 2.08 (s, 3, CH$_3$), 3.12 (s, 3, —OCH$_3$), 4.22 (s, 2, —C$\underline{H}_2$OCH$_3$), 3.92 (m, 2, C$_4$—H), 4.82 (m, 1, C$_3$—H), and 7.2 (b, ArH).

EXAMPLE 11

Benzhydryl 2-[3-[D-2-(4-hydroxyphenyl)-2-tert-butoxybutoxycarbonylaminoacetamido]-2-oxoazetidin-1-yl]-3-methyl-4-methoxy-2-butenoate In accordance with the procedures described in Example 5 above 1 mmol benzhydryl 2-(3-amino-2-oxoazetidin-1-yl)-3-methyl-4-methoxy-3-butenoate hydrochloride was acylated using the benzotriazolyl ester of D-2-(4-hydroxyphenyl)-2-tert-butoxycarbonylaminoacetic acid as the acylating agent to provide 600 mg of the title product: nmr (CDCl$_3$) δ 1.42 (s, 9, tert-butyl), 2.00 (s, 3, CH$_3$), 3.20 (s, 3, —OCH$_3$), 4.33 (s, 2, —C$\underline{H}_2$OCH$_3$), 3.58 (m, 2, C$_4$—H), 4.97 (m, 1, C$_3$—H), 5.03 (s, 1, side chain C$\underline{H}$), and 7.2 (b, ArH).

EXAMPLE 12

2-[3-[D-2-(4-Hydroxyphenyl)-2-aminoacetamido]-2-oxoazetidin-1-yl]-3-methyl-4-methoxy-2-butenoic acid trifluoroacetic acid salt The product from Example 11 was dissolved in ½ ml of anisole at 0° and 1½ ml of cold trifluoroacetic acid was added. The solution was stirred for ½ hour after which time 20 ml of hexane was added. The solvents were then removed under reduced pressure. The residue thereby obtained was washed with ether and dried to provide 220 mg of the title product: nmr (DMSO d-6) δ 1.93 (s, 3, CH$_3$), 3.28 (s, 3, —OCH$_3$), 4.33 (s, 2, —C$\underline{H}_2$OCH$_3$), 3.58 (m, 2, C$_4$—H), 4.87 (m, 1, C$_3$—H), 4.99 (s, 1, side chain —CH—) and 7.2 (b, ArH).

EXAMPLE 13

Benzhydryl 2-(3-phenoxyacetamido-2-oxoazetidin-1-yl)-3-methyl-4-(1-methyl-5-tetrazolylthio)-2-butenoate To a stirred solution of 563 mg (1 mmol) of benzhydryl 2-(3-phenoxyacetamido-2-oxoazetidin-1-yl)-3-methyl-4-bromo-2-butenoate in a mixture of 2 ml propylene oxide and 4 ml of dimethylformamide at 0° was added 128 mg (1.1 mmol) of 1-methyl-5-mercapto-1,2,3,4-tetrazole. After 1 hour at 0°, the solution was added to a large amount of ethyl acetate and washed thoroughly with brine. The ethyl acetate layer was dried and evaporated to provide the title product: nmr (CDCl$_3$) δ 2.20 and 2.37 (s, 3, CH$_3$), 3.83 and 3.86 (s, 3, N—CH$_3$), 4.43 (s, 2, —C$\underline{H}_2$S—), 5.88 (d, 2, C$_4$—H), 5.50 (q, 1, C$_3$—H), 4.57 (s, 2, side chain CH$_2$) and 7.2 (b, ArH).

EXAMPLE 14

2-(3-Phenoxyacetamido-2-oxoazetidin-1-yl)-3-methyl-4-(1-methyl-5-tetrazolylthio)-2-butenoic acid The product from Example 13 above was dissolved in 1 ml of anisole. At 0° 1 ml of trifluoracetic acid was added. After 15 minutes at 0°, hexane was added. The solvents were removed under reduced pressure. Ether was added to the residue. The resulting slurry was filtered to provide 210 mg (53% from bromo derivative) of the title product: nmr (CDCl$_3$) δ 2.10 and 2.27 (s, 3, CH$_3$), 3.92 (s, 3, N—CH$_3$), 4.3 (m, 2, —C$\underline{H}_2$S), 3.50 (m, 2, C$_4$—H), 5.00 (m, 1, C$_3$—H), 4.50 (s, 2, side chain CH$_2$) and 7.2 (b, ArH).

EXAMPLE 15

Benzhydryl 2-(3-phenoxyacetamido-2-oxoazetidin-1-yl)-3-methyl-4-formyloxy-2-butenoate To a solution of 0.65 ml (5 mmol) of tetramethyl guanidine and 0.15 ml (5 mmol) of formic acid in 20 ml of methylene chloride at 0° was added 563 mg (1 mmol) of benzhydryl 2-(3-phenoxyacetamido-2-oxoazetidin-1-yl)-3-methyl-4-bromo-2-butenoate. The reaction mixture was stirred for 15 minutes at 0° and 2 hours at room temperature. Methylene chloride (100 ml) was added. The resulting solution was washed with brine (3X), dried, and evaporated in vacuo to dryness to provide the title product: nmr (CDCl$_3$) δ 2.17 and 2.05 (s, 3, CH$_3$), 4.92 (m, 2, —C$\underline{H}_2$O—), 3.60 (m, 2, C$_4$—H), 4.98 (m, 1, C$_3$—H), 4.48 (s, 2, side chain CH$_2$), 7.2 (b, ArH) and 8.03 (s, 1, —OC$\underline{H}$O).

EXAMPLE 16

Benzhydryl 2-(3-phenoxyacetamido-2-oxoazetidin-1-yl)-3-methyl-4-hydroxy-2-butenoate To 6 ml of 0.1 N aqueous sodium hydroxide at 0° was added a solution of 338 mg (0.6 mmol) of benzhydryl 2-(3-phenoxyacetamido-2-oxoazetidin-1-yl)-3-methyl-4-formyloxy-2-butenoate in 10 ml of cold THF. After 30 minutes, ethyl acetate was added. The organic layer was separated, washed with dilute acid and brine, dried, and evaporated in vacuo to dryness to provide 250 mg of a multi-component mixture. Separation by preparative thin layer chromatography (silica gel plates developed with 3:1/ethyl acetate:hexane) provided 35 mg of the title product: nmr (CDCl$_3$) δ 2.28 (s, 3, CH$_3$), 4.72 (s, 2, —C$\underline{H}_2$OH), 3.60 (m, 2, C$_4$—H), 5.02 (m, 1, C$_3$—H), 4.55 (s, 2, side chain CH$_2$), and 7.2 (b, ArH).

EXAMPLE 17

2-[3-[D-2-(4-hydroxyphenyl)-2-[(N,N'-dimethylureido)-carbonylamino]acetamido]-2-oxoazetidin-1-yl]-3-methyl-4-methoxy-2-butenoic acid To a solution of 160 mg (0.34 mmol) of 2-[3-[D-2-(4-hydroxyphenyl)-2-aminoacetamido]-2-oxoazetidin-1-yl]-3-methyl-4-methoxy-2-butenoic acid trifluoroacetic acid salt in 2 ml of acetonitrile was added 1 ml of propylene oxide and 0.33 ml bistrimethylsilylacetamide. Then 51 mg (0.34 mmol) of N,N'-dimethylureidocarbonyl chloride was added at 0°. After stirring the reaction mixture for 2 hours at room temperature a large amount of ethyl acetate was added. The resulting mixture was then layered with water, the pH of which was adjusted to 8.5. The aqueous layer was separated, layered with ethyl acetate and stirred as the pH of the aqueous layer was adjusted to 2.0. The organic layer was separated, dried, and evaporated in vacuo to dryness. The residue thereby obtained was slurried with ether, filtered, and dried. Yield—57 mg of the title product: nmr (acetone D-6) δ 3.22 (s, 3, —OCH$_3$), 4.60 (s, 2, —C$\underline{H}_2$OCH$_3$), 3.8 (m, 2, C$_4$—H), 5.03 (m, 1, C$_3$—H), 5.38 (3, 1, side chain C$\underline{H}$), and 7.2 (b, ArH).

Note: A second crop (70 mg) of the title product precipitated from the etheral filtrate. Total yield—127 mg.

EXAMPLE 18

Benzhydryl 2-(3-phenoxyacetamido-2-oxoazetidin-1-yl)-3-methyl-4-pyridinium-2-butenoate bromide To a solution of 563 mg (1 mmole) of benzhydryl 2-(3-phenoxyacetamido-2-oxoazetidin-1-yl)-3-methyl-4-bromo-2-butenoate in 1 ml of dry tetrahydrofuran at room temperature was added 0.079 ml (1 mmol) of pyridine. The product precipitated from the reaction mixture as it was stirred overnight. After diethyl ether was added to the reaction mixture it was filtered to provide 608 mg of the title product as a tan powder: nmr (DMSO d-6) δ 1.95 (s, 3, CH$_3$), 3.9 (m, 2, azetidinone C-4 H), 4.6 (s, 2, —OCH$_2$—), 5.1 (m, 1, azetidinone (C-3 H9, 5.8 (s, 2, allylic CH$_2$) and 6.8-9.6 (NH, ArH).

EXAMPLE 19

2-(3-Phenoxyacetamido-2-oxoazetidin-1-yl)-3-methyl-4-pyridinium-2-butenoic acid trifluoroacetate The benzhydryl ester from Example 18 was added to 1 ml of anisole under nitrogen. After cooling to ice-water bath temperature 1 ml. of trifluoroacetic acid was added. The ester slowly dissolved. After ten minutes the reaction mixture was diluted with hexane and evaporated in vacuo to provide an oil. The oil thereby obtained was taken up in hexane; the resulting solution was evaporated in vacuo to provide a resinous product. Trituration with diethyl ether provided 416 mg of the title product as a tan amorphous solid: nmr (DMSO d-6) δ 1.95 (s, 3, CH$_3$), 3.82 (m, 2, azetidinone C-4 H), 4.62 (s, 2, —OCH$_2$—), 5.0 (m, 1, azetidinone C-3 H), 5.62 (m, 2, allylic CH$_2$), 6.8-8.7 (ArH, NH).

We claim:
1. A compound of the formula

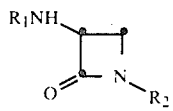

wherein R$_2$ is a group of the formula

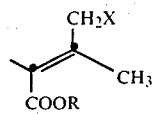

wherein R is a hydrogen or a carboxylic acid ester protecting group and
X is chloro, bromo, C$_1$-C$_3$ acyloxy, hydroxy, C$_1$-C$_4$ alkoxy, benzyloxy, or a group of the formula

wherein R$_3$ is C$_1$-C$_4$ alkyl, or phenyl, and
wherein R$_1$ is hydrogen or an acyl group of the formula

wherein R$_5$ is
(a) hydrogen, C$_1$-C$_4$ alkyl, halomethyl or phenyl;
(b) benzyloxy, 4-nitrobenzyloxy, 2,2,2-trichloroethoxy, tert-butoxy, or 4-methoxybenzyloxy;
(c) an arylalkyl group of the formula

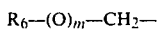

wherein m is 0 or 1 and R$_6$ is 1,4-cyclohexadienyl, phenyl or phenyl substituted with 1 or 2 substituents independently selected from the group consisting of halo, hydroxy, nitro, cyano, trifluoromethyl, C$_1$-C$_4$ alkyl and C$_1$-C$_4$ alkoxy;
(d) a substituted arylalkyl group of the formula

wherein R$_7$ is R$_6$ as defined above, 2-thienyl or 3-thienyl and W is hydroxy, protected hydroxy, carboxy, protected carboxy, amino, protected amino or a group of the formula

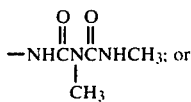

(e) a heteroaryl methyl group of the formula

wherein R$_8$ is 2-thienyl, 3-thienyl, 2-furyl, 2-thiazolyl, 5-tetrazolyl, 1-tetrazolyl or 4-isoxazolyl,
and when R$_1$ is hydrogen, the hydrochloride acid addition salts of the amines represented thereby, and when R is hydrogen the pharmaceutically acceptable salts of the acids represented thereby.

2. The compound of claim 1 wherein R$_2$ is a group of the formula

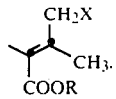

3. The compound of claim 2 wherein $R_1$ is hydrogen.

4. The compound of claim 2 wherein R is tert-butyl, 4-methoxybenzyl or diphenylmethyl.

5. The compound of claim 2 wherein R is hydrogen.

6. The compound of claim 2 wherein $R_1$ is an acyl group of the formula $$\underset{R_5C-}{\overset{O}{\underset{\|}{}}}.$$

7. The compound of claim 6 wherein $R_5$ is an arylalkyl group of the formula $R_6-(O)_m-CH_2-$.

8. The compound of claim 7 wherein $R_6$ is phenyl.

9. The compound of claim 6 wherein $R_5$ is a substituted arylalkyl group of the formula $$\underset{W}{\overset{R_7CH-}{\underset{|}{}}}$$

10. The compound of claim 9 wherein W is a group of the formula $$-\underset{CH_3}{\underset{|}{NHCNCNHCH_3}}\overset{O\ \ O}{\overset{\|\ \ \|}{}}.$$

11. The compound of claim 6 wherein X is chloro or bromo.

12. The compound of claim 6 wherein X is $C_1-C_4$ alkoxy.

13. The compound of claim 6 wherein X is a group of the formula $-SR_3$.

14. The compound of claim 6 wherein X is hydroxy or $C_1-C_3$ acyloxy.

* * * * *